US00PP10832P

United States Patent [19]

Deutscher et al.

[11] Patent Number: Plant 10,832

[45] Date of Patent: Mar. 23, 1999

[54] APPLE TREE NAMED 'CUMBERLAND SPUR'

[76] Inventors: Robert L. Deutscher; Carol J. Deutscher, both of 6236 Co. Rd. 39, Fackler, Ala. 35746

[21] Appl. No.: 819,883

[22] Filed: Mar. 18, 1997

[51] Int. Cl.[6] ..... A01H 5/00

[52] U.S. Cl. ..... Plt./35

[58] Field of Search ..... Plt./34.1, 35

[56] References Cited

U.S. PATENT DOCUMENTS

P.P. 4,839 4/1982 Evans et al. ..... Plt./35

P.P. 5,547 9/1985 Hare ..... Plt./35

*Primary Examiner*—Howard J. Locker

[57] ABSTRACT

A new and distinct variety of apple *Malus domestica* tree called 'Cumberland Spur' is a mutation (limb sport) of 'Oregon Spur' variety, U.S. Plant Pat. No. 2,816, and is characterized by its fruits which develop early, intense, near 100% red over color as a blush (rather than the characteristic striped pattern of its parent) at harvest time. 'Cumberland Spur' blooms 2 to 3 days later than 'Oregon Spur' and is ready for harvest 10 to 14 days earlier.

4 Drawing Sheets

SUMMARY OF THE INVENTION

The present invention relates to a new and distinct apple variety. The new cultivar is designated 'Cumberland Spur' and is a limb sport of an 'Oregon Spur' tree. It was discovered as a limb sport off the central leader of an 'Oregon Spur' (U.S. Plant Pat. No. 2816) tree in the originators' commercial orchard because fruits on the limb in question developed such intense and early red over color compared to its parent's.

Following the discovery by the originators at Crow Mountain Orchards, it was asexually reproduced (on M-26 rootstock) in 1989 and planted on the originators property, Crow Mountain Orchards, near Fackler (Jackson County), Ala. in 1990. Fruiting was first observed on reproduced plants in 1992. Subsequent propagation of additional plants has permitted evaluation of plant and fruiting characteristics over a range of trees aged 3 to 7 years. Asexual propagation by budding shows that the unique combination of early coloring, high quality fruit and very desirable spur-type growth characteristics come true to form and are readily transmitted through succeeding propagations.

BRIEF DESCRIPTION OF THE DRAWINGS

The accompanying photographs show typical specimens of the fruit and fruits on young trees as depicted in colors as true as reasonable possible using color print illustrations.

Figure 1:
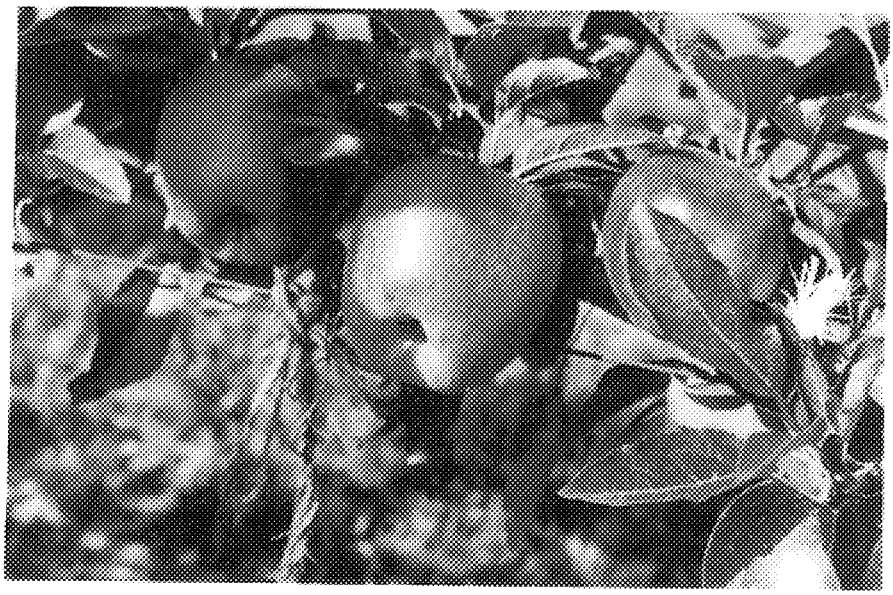
FIG. 1: shows a closeup of typically, mature fruits of 'Cumberland Spur' at harvest time Aug. 31, 1995. This photograph also depicts the spur bearing habit, surface finish of unpolished, mature fruit, the distribution of lenticels on the fruit skin along with the blossom end characteristics of the fruit of this tree. Also depicted are foliage density, color of top and bottom surfaces of leaves and leaf petiole and mid-rib coloration.
Figure 2:
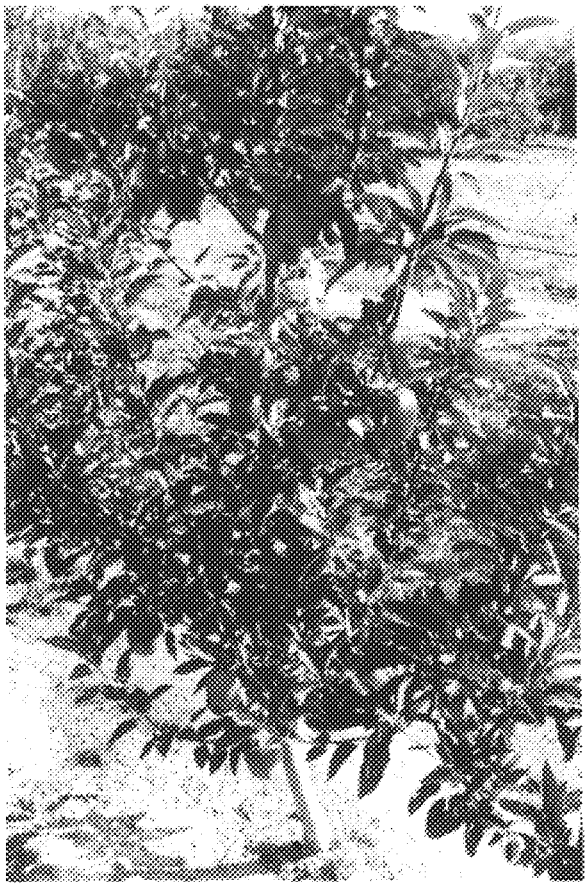
FIG. 2: shows the spur-type growth and precocious fruiting habits of a 4th leaf 'Cumberland Spur' tree on M-26 rootstock at harvest time Aug. 31, 1995. Scaffold development of a typical specimen of the tree is depicted along with adaptability of tree to trellis production using the specified rootstock.

Note that 'Cumberland Spur' fruit and fruit stems are a pronounced red coloration while fruits of 'Scarlet Spur' and 'Hared' maintain a strong green coloration. However, some fruits on 'Scarlet Spur' exhibit a partial pattern of red streaking (not a blush pattern like 'Cumberland Spur') on the sunny side of the fruit. Fruit stems of 'Hared' are green while those of 'Scarlet Spur' have green to reddish coloration. Red fruit color develops later in the season for 'Scarlet Spur' and 'Hared' under southeastern conditions.

DETAILED DESCRIPTION

The distinctive characteristics of this new apple cultivar as described below were observed in the 1995 and 1996 growing seasons on the originators property in Fackler. Trees were in the 6th and 7th growing seasons.

The color designations hereinafter set forth are according to the Munsell Color System using a Minolta CAT/HS 1000 color meter. All color measurements of fruit skin, flesh and seeds were made using fruits which were harvested at proper stage for commercial harvest and held in conventional (32° to 35° F.) cold storage for less than one week. The term "proper stage" implies fruits were tree ripened and may be eaten as soon as harvested (no storage needed) which contrasts with fruit destined for long term storage which are harvested less ripe and contain high levels of starch. Commercial growers in Alabama harvest their apples at the tree ripe stage. At this stage of ripeness 'Cumberland Spur' fruits were fully red (essentially 100% blush). Soluble solids at this stage was quite high (14.6% equivalent). Other Red Delicious varieties at this site and farms in the area harvested at a similar level of tree ripeness usually had soluble solids of 11.0 to 13.0%. The parent ('Oregon Spur') of this sport and 'Hared' commonly had levels of 11.0 to 13.0% soluble solids when harvested tree ripe at this same location. 'Scarlet Spur' averaged 12.0 to 12.5% soluble solids in experimental substation orchards in the same area of the state.

'Cumberland Spur' is similar to its parent 'Oregon Spur' in general but is distinctively different in at least seven areas. Fruits of 'Cumberland Spur', (1) develop intense red over color (blush) 4 weeks earlier than 'Oregon Spur', (2) develop essentially a 100% (4.6R3/6.6) red over color that almost completely masks the yellow under color (7.5YR6/5). This 100% blush development is achieved under very difficult southeastern environmental conditions, where red delicious cultivars are known for developing mediocre to less than ideal red blush. Red delicious cultivars grown in the US usually develop more intense red blush in the northwestern growing areas such as Washington state. (3) The red over color of the fruit skin develops as a blush on 'Cumberland Spur' while its parent develops a red striped pattern. The fourth (4) distinct feature of 'Cumberland Spur' compared to its parent is superior flavor. A number of informal taste tests conducted at Alabama grower meetings over a 3-year period, clearly revealed a distinct preference for 'Cumberland Spur' over other red delicious cultivars, including 'Oregon Spur' and 'Red Chief' (Campbell strain, U.S. Plant Pat. No. 3,578).

As indicated above in describing "proper stage" for harvest, 'Cumberland Spur' has a higher sugar content when harvested tree ripe than other Red Delicious varieties including its parent 'Oregon Spur','Scarlet Spur' and 'Hared'. This is primarily responsible for its superior flavor. Sweetness is sometimes associated with water core development. However, since 'Cumberland Spur' began fruiting on site in 1992, no water core development has been found in fruits.

Fruits of 'Cumberland Spur' have somewhat superior on tree storage characteristics than its parent 'Oregon Spur'. At harvest, fruits of 'Cumberland Spur' usually hold well on the tree for an additional 7 to 10 days compared to its parent.

The fifth difference involves the bloom date. 'Cumberland Spur' flowers approximately two to three days later than its parent ('Oregon Spur'). This affords at least some added protection against late freezes.

A sixth area where 'Cumberland Spur' stands out is in the packout at harvest. Based on records at Crow Mountain Orchards, the average packout for 'Cumberland Spur' since 1992 has been 90% while that of 'Hared' approaches 80% and the parent 'Oregon Spur' 65%. Further, no 'Cumberland Spur' fruit were eliminated because of lack of red color while this was not true for 'Hared' and 'Oregon Spur'.

It is the seventh difference, coloration of young fruits, that perhaps clearly separates 'Cumberland Spur' from 'Oregon Spur's' other two similar sports, 'Scarlet Spur' and 'Hared'. Although some small differences in flower coloration is evident among these three selections at anthesis it is difficult to quantify. All selections have pink flower buds and various shades of pink on white petals.

Figure 3:
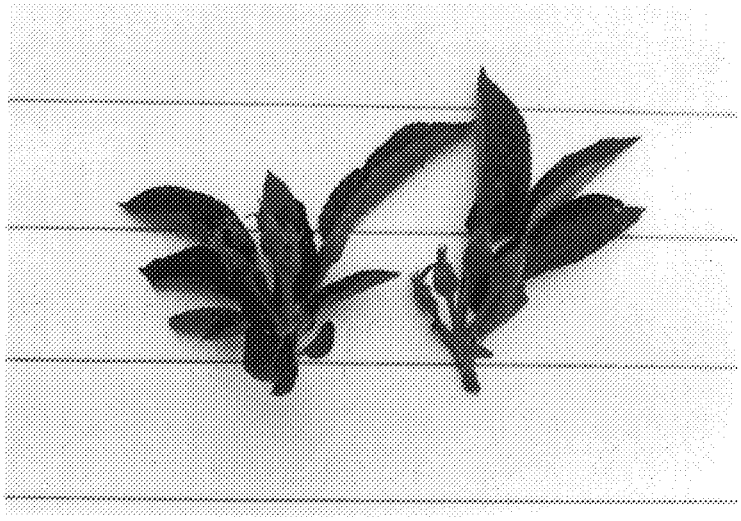
FIG. 3: shows young fruits (10 to 14 days past bloom) of 'Hared' (U.S. Plant Pat. No. 5,547) (left) and 'Cumberland Spur' (right). Note 'Cumberland Spur' fruits and fruit stems have pronounced red coloration while 'Hared' fruits have slight red coloration and green fruit stems.

However, differences definitely exist in the level of red color (anthocyanin pigment) in developing fruits and fruit stems (peduncles) among 'Cumberland Spur', 'Hared' and 'Scarlet Spur'. In FIG. 3 it is evident that 'Hared' fruits within 10 to 14 days of bloom have slight red coloration and green fruit stems while 'Cumberland Spur' has red fruit and red fruit stems.

Figure 4:
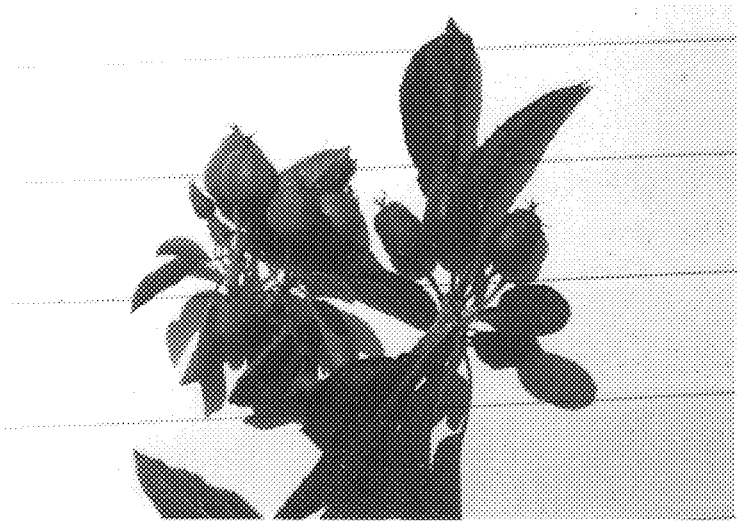
FIG. 4 shows young fruits (4 to 5 weeks past full bloom) of 'Hared' (left) and 'Cumberland Spur' (right).
Figure 5:
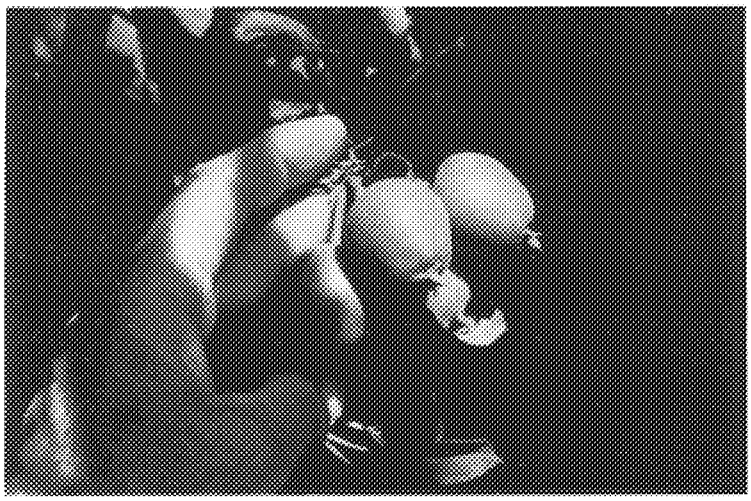
FIG. 5 shows young fruits (4 to 5 weeks past full bloom) of 'Scarlet Spur' (U.S. Plant Pat. No. 4,839).

The color differences referred to in FIG. 3 are more readily noticeable at 4 to 5 weeks past full bloom as illustrated in FIG. 4 and FIG. 5. Note that only 'Cumberland Spur' has both red fruit and red fruit stems while 'Hared' has green fruit and green fruit stems. 'Scarlet Spur' has green to red fruit stems but mostly green fruit (some fruit exhibit varying levels of red, streaking-type coloration on sunny side of fruit).

These same color differences are not found in leaf stems and mid-ribs in early spring. The developing leaf stems (petioles) and mid-ribs of 'Cumberland Spur' are mostly green with only a hint of red coloration. However, at this site, the other Red Delicious varieties such as 'Oregon Spur' and 'Hared' tend to have similar coloration of leaf stems and mid-ribs. 'Scarlet Spur', grown in north and central Alabama, also has green leaf stems and mid-ribs.

Southeastern produced red delicious are often not very typey (developed calyx lobes) compared to those grown in Washington state. However, use of a growth regulator can improve typiness. Over the 5 years of evaluation thus far 'Cumberland Spur' has produced fruit much more typey (similar to northwestern fruit) than average for the Southeast.

When compared with 'Oregon Spur' and 'Red Chief' (Campbell strain), 'Cumberland Spur' stored equally as well (3 to 4 months) in conventional refrigeration (32° to 35° F.) and fruit flesh was as firm or firmer. When grown under similar cultural conditions, fruit size of 'Cumberland Spur' compared well with other red delicious cultivars. Pack out of 90% or better is common for 'Cumberland Spur' because of superior color, and good size. This level of packout exceeds that of all other red delicious cultivars grown at Crow Mountain Orchards.

Tree: Spur-type growth habit; low to medium vigor, somewhat spreading habit; fruit production mostly on spurs; medium to high spur density; branching characteristics are similar to those of 'Scarlet Spur'; branching occurs quite readily providing a growth habit and branching characteristics equal to or slightly greater than its parent, 'Oregon Spur' and fruiting within two years of planting, on trees 5 years of age on M-26 rootstock (grown on trellis) height is approximately 7 feet with a canopy width of 3½ feet; annual terminal growth is 15 to 24 inches; Under good management trees are annual bearing; at least a medium thinning requirement is needed on M-26 rootstock to balance fruit size and tree growth; overall annual productivity is equal to 'Oregon Spur'; bud hardiness and ability to crop following spring freezes is similar to 'Oregon Spur'.

Flower: Color of buds just before opening is deep pink to rose; flowers are large size (like parent 'Oregon Spur') but are deeper pink than parent (more like pinkish to red color of 'Red Chief' (Campbell strain) flowers. At anthesis, flowers have moderately cupped shape with margins of adjacent petals usually touching.

Leaf: Medium to slightly late in bud break; mature leaves which comprise the midsection of non-fruiting shoots during the middle of growing season were of medium size and shape similar to its parent 'Oregon Spur', length 3.7 to 4.1 inches; width 1.8 to 2.0 inches; medium length/width ratio of blade; concave shape in cross-section; margin has fine to medium serrate indention; medium glossiness on upper side; weak to medium pubescence on lower side; petiole medium in length and thickness; small stipule size.

Fruit:

*Size.*—Large: length 3.1 inches, width 3.2 inches, average weight per fruit—8.5 ounces.

*Shape.*—Mostly oblong, calyx lobes somewhat prominent.

*Eye.*—Closed, medium size.

*Eye basin.*—Medium depth and width.

*Sepals.*—Medium length; touching at base.

*Stalk.*—Medium to long; medium thickness

*Stalk cavity.*—Medium depth and width.

*Skin.*—Smooth surface; no cracking tendency; medium skin thickness; yellow ground color (7.5YR6/5) but covered almost totally with over color; difficult to obtain color reading because of predominance of red over color.

*Over color* (*blush*).—Essentially 100% red over color (4.6R3/6.6); low amount of russet around stalk.

*Lenticels.*—Small size.

*Flesh.*—Firm (average of 17 psi at harvest); firmer than 'Oregon Spur' and 'Red Chief' (Campbell strain) when grown under cultural program at Fackler; flesh is yellowish white to white (8.2Y8.2/2.5) which contrasts with parent, 'Oregon Spur' (mostly yellowish white) and 'Starkrimson' (mostly greenish white).

*Flavor.*—Excellent dessert quality but good sweet/acid balance, soluble solids (% glucose equivalent) before storage is 14.6.

*Calyx tube.*—Short to medium length, medium width; U or V shaped.

*Distinctiveness of core line.*—Medium when observed in cross section.

*Central cavity.*—Absent in cross section.

*Ripening.*—At Crow Mountain Orchards in Fackler, harvest was between Aug. 24 and Aug. 31 in 1995. Note: this site is at an elevation exceeding 1700 feet, which is high compared to other production areas in Alabama.

*Seed.*—Medium size; brown color when dry (2.5YR2.5/3).

We claim:

1. A new and distinct variety of apple tree which is a mutation (limb sport) of the 'Oregon Spur', substantially as shown and described; and characterized by its more intense and earlier red coloring, near 100% blush over color development, earlier harvest, superior flavor, slightly later flowering and greater packout than its parent.

* * * * *